United States Patent

Warolin et al.

[11] 4,153,729
[45] May 8, 1979

[54] THERAPEUTICALLY USEFUL CYSTEINOL AND HOMOCYSTEINOL DERIVATIVES

[75] Inventors: Christian J. M. Warolin; Pierre Muller; Roger Zaoui, all of Paris, France

[73] Assignee: Recherches Pharmaceutiques et Scientifiques, France

[21] Appl. No.: 875,571

[22] Filed: Feb. 6, 1978

[30] Foreign Application Priority Data

Feb. 7, 1977 [FR] France .................... 77 03308

[51] Int. Cl.² .................... A61K 31/13; C07C 149/42; C07C 91/12
[52] U.S. Cl. .................................................. 424/325
[58] Field of Search ........................................ 424/325

[56] References Cited
U.S. PATENT DOCUMENTS 3,892,865  7/1975  Roehm .................................. 424/325

*Primary Examiner*—Frederick E. Waddell
*Attorney, Agent, or Firm*—Gordon W. Hueschen

[57] ABSTRACT

Compounds of the formula

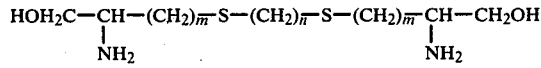

(in which n is equal to 0 or represents a whole number from 1 to 10 and m represents the number 1 or 2) and their pharmacologically acceptable salts are prepared and have therapeutic, in particular hypolipemic, activity.

8 Claims, No Drawings

THERAPEUTICALLY USEFUL CYSTEINOL AND HOMOCYSTEINOL DERIVATIVES

This invention relates to bis-alkylene cysteinols and bis-alkylene homocysteinols, a process for their preparation and their use as therapeutically active substances, notably with hypolipemic activity, the compounds being in the form of their base or pharmacologically acceptable salt.

The compounds according to the invention correspond to the general formula I

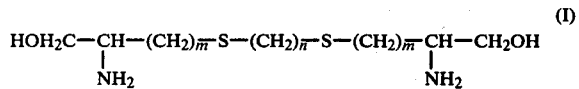

(I)

in which n is equal to 0 or represents a whole number from 1 to 10 and m represents the number 1 or 2.

The compounds of formula I (in which n represents a whole number from 1 to 10) may be prepared by reaction of an alkane dihalide of formula II $$X-(CH_2)_n-X \qquad (II)$$

(in which X represents a halogen atom and n represents a whole number between 1 and 10) with S-benzylcysteinol or S-benzylhomocysteinol of the respective formulae IIIa and IIIb

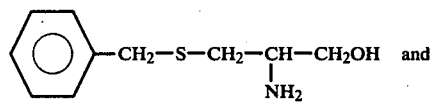

(IIIa)

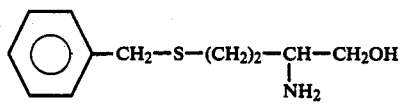

(IIIb)

in liquid ammonia in the presence of an alkaline amide, such as sodium amide. The dihalide of formula II can be used pure or in solution in a solvent such as diethyl ether; it may be used in stoichiometric proportion or in excess, for an example an excess amounting up to 100%. Preferably in the dihalide X represents a bromine atom.

The separation of the reaction products may be effected in known fashion: evaporation of the ammonia, extraction of the organic phase and purifications.

If necessary or desired the product obtained may be converted into a pharmacologically acceptable salt in known manner.

Compounds of formula I in which n equals O may be prepared by conversion of the S-benzyl derivatives of formula IIIa or IIIb into a thiol and then oxidation with air to obtain the corresponding disulphide.

The S-benzyl derivatives are suitably converted into the thiol in liquid ammonia in the presence of sodium amide. The thiol obtained may suitably be oxidized by bubbling air into an aqueous solution of the thiol in the presence of ferric chloride.

The invention provides a pharmaceutical composition comprising, as active ingredient, a compound of formula I or a pharmacologically acceptable salt thereof together with a pharmacologically acceptable carrier or diluent. The compounds of formula I are used in pharmaceutically acceptable purity, with a pharmaceutically acceptable carrier or diluent selected generally from the group consisting of solid extenders, ingestible containers of capsules and cachets, non-solvent liquid media, solvent liquid media comprising a solvent and at least one additive selected from the group consisting of sweetening, flavouring, colouring, preserving and surface active agents, and sterile liquid media.

Preferably the composition is in an orally administrable form, most preferably a form permitting administration of doses of from 5 to 30 mg/kg per day.

The invention further provides a method of treating a human patient which method comprises administering to the patient a compound of formula I or a pharmacologically acceptable salt thereof.

S-benzylcysteinol of formula IIIa used as a starting material, may be obtained in the following fashion in three stages:

(1) Preparation of S-benzylcysteine according to the method described by M. D. Armstrong, Journal of Organic Chemistry, 16, 749–53 (1951).

(2) Preparation of the hydrochloride and the ethyl ester base of S-benzylcysteine according to J. C. Crawall, D. F. Elliot and K. C. Hooper, Journal of the Chemical Society, 4066–68 (1956).

(3) Preparation of S-benzylcysteinol by reductive saponification in the presence of lithium aluminium hydride or triethyllithium borohydride; this compound has been obtained in impure form in the form of the oxalate by J. C. Crawall, same reference as above.

S-benzylhomocysteinol of formula IIIb can be prepared according to analogous stages to those described above. The first, that is the preparation of the S-benzylcysteine, is described in Biochemical Preparations 5, 87.

The following Examples 1 to 14 illustrate the preparation of particular compounds of the invention. Examples A and B illustrate the preparation of starting materials.

EXAMPLE A

S-benzylcysteinol

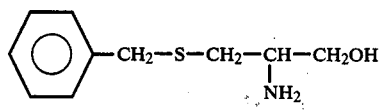

In a three necked 2000 ml. flask provided with a sealed mechanical stirrer, a coolant with calcium chloride protection, and a bromine ampoule protected from atmospheric humidity there are placed:

350 ml of rectified anhydrous ether on LiAlH$_4$, 15.8 g of LiAlH$_4$ (i.e. four times the theoretical quantity which is half a mole of LiAlH$_4$ per mole of the ester).

The suspension is brought to reflux with stirring. The solution of the base ester (50.3g) in anhydrous ether is introduced at a suitable speed to maintain the reflux.

The boiling of the reaction mixture is continued for 10 minutes after the end of the addition of the solution of the ester base.

After cooling, the excess of lithium aluminium hydride is destroyed by the minimum quantity of water added drop by drop.

The alumina is removed and washed with ether.

The ethereal solutions are distilled. The residue crystallises.

29.5 g of white crystals are obtained.

Yield: 71.2%—Melting Point: 38° to 40° (Tottoli).

| Analysis for $C_{10}H_{15}ONS$ = 197.29 | | | |
|---|---|---|---|
| C% | calculated | 60.87 | found | 61.19 to 61.27 |
| H | " | 7.66 | found | 7.81 to 7.80 |
| N | " | 7.09 | " | 7.01 to 7.01 |
| S | " | 16.25 | " | 16.16 |

The S-benzylcysteinol may be purified by distillation. B.Pt. 142° to 144° C. under 0.25 mm mercury. Melting point: 44° (Tottoli).

| Analysis for $C_{10}H_{15}ONS$ = 197.29 | | | |
|---|---|---|---|
| C% | calculated | 60.87 | found | 60.78 |
| H | " | 7.66 | " | 7.98 |
| N | " | 7.09 | " | 7.10 |
| S | " | 16.25 | " | 16.51 |

IR SPECTRUM: $NH_2$ band at 1600 cm$^{-1}$; $CH_2OH$ band at 1050 cm$^{-1}$.

NMR SPECTRUM: Reference Tetramethylsilane (TMS)

—C$\underline{H_2}$—S—  2.5 p.p. m (m)
—C$\underline{H}$—  2.9 p.p. m (m)
  |
HO—C$\underline{H_2}$—  3.48 p.p. m (m)
S—C$\underline{H_2}$—Cl  3.67 p.p. m (s)

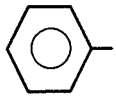 7.3 p.p. m (s)

T.L.C. (Thin layer chromatography using silica gel prepared plates 60F254, Ex. Merck; H = 8 cm)
Solvent:  Propanol  60
  NH$_4$OH  30
  Ethylene Diamine  10
Developer:  ninhydrin-I$_2$.

EXAMPLE B

S-benzylhomocysteinol (a) Ethyl 2-amino-4-benzylthiobutanoate

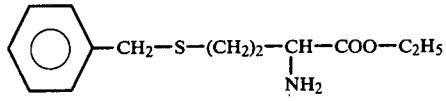

300 g of S-benzylhomocysteine are placed in suspension with stirring in 3,900 liters of absolute ethanol. The reaction mixture is refluxed for 5 hours in the presence of a rapid current of dry HCl.

The solution is decolourised by carbon black and the filtrate reduced to dryness. The composition taken up in 1200 ml of ether and 135 g of triethylamine is stirred for 1 hour at the laboratory temperature. Insolubles are washed by diethyl ether with stirring. The ethereal filtrates are mixed and reduced to dryness.

The residue, 315.4 g, is a yellow oil which is rectified under 0.8 mm Hg.
Boiling Point: 170° to 178° C.
Yield 71.5% ((226.2g).

| Analysis for $C_{13}H_{19}O_2NS$ = 253.36 | | | |
|---|---|---|---|
| C% | calculated | 61.63 | found | 61.66 to 61.72 |
| H | " | 7.56 | " | 7.83 |
| N | " | 5.53 | " | 5.72 to 5.81 |
| S | " | 12.66 | " | 12.59 |

IR SPECTRUM: $NH_2$ band: 1.580 cm$^{-1}$; COOR band: 1.748 cm$^{-1}$.

| T.L.C. (Prepared silica gel plates 60F254; H = 8 cm) | |
|---|---|
| Butanol | 40 |
| Acetic Acid | 10 |
| Ethylene Diamine | 50 |
| Developers:ninhydrin - | I$_2$ |

Hydrochloride (Purified in ethanol/diethyl ether). Melting Point: 62.5° to 63.5° (Tottoli).

| Analysis for $C_{13}H_{20}O_2NSCl$ = 289.82 | | | |
|---|---|---|---|
| C% | calculated | 53.87 | found | 53.79 to 53.78 |
| H | " | 6.95 | " | 7.09 |
| N | " | 4.83 | " | 4.84 to 4.88 |
| S | " | 11.06 | " | 11.02 |

NMR SPECTRUM - Reference TMS

—C$\underline{H_2}$—CH$_3$  4.3 p.p.m.(m)     —S—C$\underline{H_2}$—  2.6 p.p.m.(m)
—C$\underline{H_3}$  1.3 p.p.m.(t)     —S—C$\underline{H_2}$—CH$_2$ 2.3 p.p.m.(m)

⟨O⟩—  7.4 p.p.m.(s)  These two latter signals form an A$_2$B$_2$ system to which is added the signal of ⟨O⟩—C$\underline{H_2}$—S—  3.8 p.p.m.(s)  —C—H—
                                              |

(b) S-benzylhomocysteinol

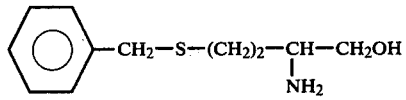

To a suspension of 43 g of LiAlH$_4$ (4 times the theoretical amount) in 1000 ml of anhydrous ether brought to reflux under mechanical agitation, there is added a solution of 144 g of the ethyl ester of the S-benzylhomocysteine in 600 ml of anhydrous ether at a speed such that the reaction mixture continues to boil. After the end of the addition, refluxing is continued for 1 hour.

The excess of LiAlH$_4$ is destroyed by water.

After extraction and washing with diethyl ether, the ethereal solutions are reduced to dryness. The residue is rectified under reduced pressure at 170° to 180° C. under 0.6 mm Hg.

A colourless oil crystallising in an ice-box was collected.

Yield 73% (88 g)—Melting point: 31° to 32° C. (Tottoli).

| Analysis for $C_{11}H_{17}ONS$ = 211.32 | | | |
|---|---|---|---|
| C% | calculated | 62.52 | found | 62.34 |
| H | " | 8.11 | " | 8.37 |
| N | " | 6.63 | " | 6.74 |

-continued

| Analysis for $C_{11}H_{17}ONS = 211.32$ | | | | |
|---|---|---|---|---|
| S | " | 15.17 | " | 15.00 |

IR SPECTRUM: NH$_2$ band: 1585 cm$^{-1}$; OH band: 1053 cm$^{-1}$.

NMR SPECTRUM-Reference TMS
Aromatics 7.4 p.p.m. (s)
3.7 p.p.m. (s)

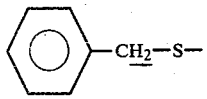—CH$_2$—S—

—S—CH$_2$—CH$_2$— 2.5 p.p.m. (m)
3 p.p.m. (massive)

—C—H

—CH$_2$OH 3.4 p.p.m. (massive)

T.L.C.: Silica gel prepared plates
60F254; H = 8 cm
Propanol 60
NH$_4$OH 30
Ethylene Diamine 10
Developers: ninhydrin - I$_2$

EXAMPLE 1

2,8-Diamino-4,6-dithia-1,9-nonanediol (Djenkolol)

HOH$_2$C—CH—CH$_2$—S—CH$_2$—S—CH$_2$—CH—CH$_2$OH
         |                                    |
         NH$_2$                                NH$_2$ 500 ml of liquefied ammonia are placed in a 1000 ml flask with three necks provided with a sealed mechanical stirrer, a potash seal and bromine ampoule. 12 g of S-benzylcysteinol are added and little by little 2.8 g (the theoretical mount) of sodium cut in to fine flakes. There is then introduced drop by drop 6.2 g dibromomethane (20% excess relative to the theoretical quantity of 5.2g). The blockage of the —SH grouping is practically instantaneous (sodium nitroprussiate test).

The excess amide is destroyed by the theoretical quantity of ammonium chloride. The ammonia is evaporated at the laboratory temperature under a weak nitrogen current. The residue is dried under vacuum and extracted three times with 200 ml of THF. The extracts are decolourised on carbon black and evaporated to dryness.

The residue is recrystallised in ethyl acetate.
Practical Yield: 58.8% (4.0 g)
Melting point: 82° to 84° (Tottoli)
The compound is soluble in the cold in water, alcohol, ether.

| Analysis for $C_7H_{18}O_2N_2S_2 = 226.35$ | | | | |
|---|---|---|---|---|
| C% | calculated | 37.14 | found | 37.25 to 37.26 |
| H | " | 8.01 | " | 8.10 |
| N | " | 12.37 | " | 12.53 to 12.56 |
| S | " | 28.33 | " | 28.35 |

IR SPECTRUM: NH$_2$ band: 1600 cm$^{-1}$; OH band: 1050 cm$^{-1}$.

NMR SPECTRUM Reference TMS
—S—CH$_2$—S— 3.9 p.p.m. (s)
—CH$_2$OH 3.6 p.p.m. (m)

—C—H
|
—CH$_2$—S— } massive from 2.5 to 3.3 p.p.m.

T.L.C. Prepared silica gel plates 60F254;
H = 8 cm
Propanol 60
NH$_4$OH 30
Ethylene Diamine 10
Developers: ninhydrin - I$_2$

EXAMPLE 2

2,11-Diamino-4,9-dithia-1,12-dodecanediol

HOH$_2$C—CH—CH$_2$—S—(CH$_2$)$_4$—S—CH$_2$—CH—CH$_2$OH.
         |                                          |
         NH$_2$                                      NH$_2$

The operational procedures described in Example 1 are used using 1,4-dibromo-butane in place of dibromomethane. The product obtained is extracted with ether and recrystallised in ethyl acetate.

Yield: 25% — Melting Point: 78° to 80° (Tottoli)
While crystals soluble in water, alcohols, ether.

| Analysis for $C_{10}H_{24}O_2N_2S_2 = 268.44$ | | | | |
|---|---|---|---|---|
| C% | calculated | 44.74 | found | 44.89 |
| H | " | 9.01 | " | 9.27 |
| N | " | 10.43 | " | 10.18 |
| S | " | 23.88 | " | 23.97 |

IR SPECTRUM: NH$_2$ band at 1600 cm$^{-1}$; OH bands at 1050 cm$^{-1}$ and 1350 cm$^{-1}$.

NMR SPECTRUM - Reference TMS
—CH$_2$—OH 3.6 p.p.m. (m)
3 p.p.m. (m)

—C—H
|

—S—(CH$_2$)$_4$—S 2.6 p.p.m. (m)
—CH$_2$—CH$_2$— 1.7 p.p.m. (m)
T.L.C. Prepared silica gel plates 60F254;
H = 8 cm
Propanol 60
NH$_4$OH 30
Ethylene Diamine 10
Developers: ninhydrin - I$_2$

EXAMPLE 3

2,13-Diamino-4,11-dithia-1,14-tetradecanediol

HOH$_2$C—CH—CH$_2$—S—(CH$_2$)$_6$—S—CH$_2$—CH—CH$_2$OH
         |                                          |
         NH$_2$                                      NH$_2$

The operational method described in Example 1 is used using 1,6-dibromo-hexane in place of dibromomethane. The product obtained is extracted with benzene and recrystallised in ethyl acetate.

Yield: 63% — Melting Point: 83° to 84° (Tottoli)
White crystals soluble in water, alcohols, ether.

| Analysis for $C_{12}H_{28}O_2N_2S_2$ | | | | |
|---|---|---|---|---|
| C% | caculated | 48.61 | found | 48.91 |
| H | " | 9.52 | " | 9.71 |

-continued

| Analysis for $C_{12}H_{28}O_2N_2S_2$ | | | | |
|---|---|---|---|---|
| N | " | 9.44 | " | 10.67 |
| S | " | 21.63 | " | 21.78 |

IR SPECTRUM: $NH_2$ band at 1600 cm$^{-1}$; $CH_2OH$ bands at 1050 cm$^{-1}$ and 1350 cm$^{-1}$.

NMR SPECTRUM - Reference TMS
| —C$\underline{H_2}$OH | 3.5 p.p.m. (m) |
| | 2.9 p.p.m. (m) |

—C—$\underline{H}$

| —CH$_2$—S—CH$_2$— | 2.6 p.p.m. (m) |
| —(CH$_2$)$_4$— | 1.5 p.p.m. (m) |

T.L.C. Prepared silica gel plates 60F254;
  H = 8 cm
Propanol      60
NH$_4$OH       30
Ethylene Diamine 10
Developers: ninhydrin - I$_2$

EXAMPLE 4

2,15-Diamino-4,13-dithia-1,16-hexadecanediol

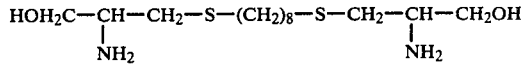

The operational method described in Example 1 is used using 1,8-dibromo-octane in place of dibromomethane. The product obtained is extracted with benzene, then recrystallised first in ethyl acetate and then in dichloro-methane.

Yield: 50% — Melting Point: 92° to 94° (Tottoli) White Crystals soluble in water, alcohols, ether.

| Analysis for $C_{14}H_{32}O_2N_2S_2$ = 324.54 | | | | |
|---|---|---|---|---|
| C% | calculated | 51.81 | found | 51.97 |
| H | " | 9.93 | " | 10.23 |
| N | " | 8.63 | " | 8.77 |
| S | " | 19.75 | " | 19.67 |

IR SPECTRUM: $NH_2$ band 1.580 cm$^{-1}$; OH bands 1.037 cm$^{-1}$ and 1.350 cm$^{-1}$.

NMR SPECTRUM - Reference TMS
| —C$\underline{H_2}$OH | 3.55 p.p.m. (m) |
| | 2.9 p.p.m. (m) |

—C—$\underline{H}$

| —CH$_2$—S— | 2.55 p.p.m. (m) |
| —4 (CH$_2$)$_6$ | 1.4 p.p.m. (m) |

T.L.C. Prepared silica gel plates 60F254;
  H = 8 cm
Propanol      60
NH$_4$OH       30
Ethylene Diamine 10
Developers: ninhydrin - I$_2$

EXAMPLE 5

2,17-Diamino-4,15-dithia-1,18-octadecanediol

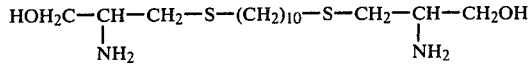

The operational method of Example 4 is used.
Melting Point: 102° to 104° (Tottoli).
Yield: 52%.

| Analysis for $C_{16}H_{36}O_2N_2S_2$ = 352.60 | | | | |
|---|---|---|---|---|
| C% | calculated | 54.50 | found | 54.57 |
| H | " | 10.29 | " | 10.65 |
| N | " | 7.94 | " | 8.20 |
| S | " | 18.18 | " | 18.21 |

IR SPECTRUM: $NH_2$ band 1577 cm$^{-1}$; OH Bands 1040 cm$^{-1}$, 1550 cm$^{-1}$.

NMR SPECTRUM - Reference TMS
| —C$\underline{H_2}$OH | 3.55 p.p.m. (m) |
| | 2.9 p.p.m. (m) |

—C—$\underline{H}$

| —CH$_2$—S—CH$_2$— | 2.55 p.p.m. (m) |
| —(C$\underline{H_2}$)$_8$ | 1.35 p.p.m. (m) |

T.L.C. Prepared silica gel playtes 60F254
  H = 8 cm
Propanol      60
NH$_4$OH       30
Ethylene Diamine 10
Developers: ninhydrin - I$_2$

EXAMPLE 6

2,7-Diamino-4,5-dithia-1,8-octanediol (Cystinol)

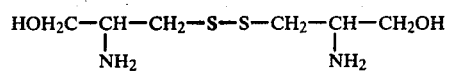

(a) CYSTEINOL 500 cm$^3$ of liquefied $NH_3$ are introduced into a 1000 cm$^3$ three necked flask provided with a sealed mechanical stirrer and a KOH guard.

15 g of S-benzylcysteinol are added and little by little 3.51 g of sodium in fine flakes (excess: 0.13 g in order that the blue coloration persists).

The excess of sodium and the sodium mercaptide of cysteinol are destroyed by 7.4 g of NH$_4$Cl.

The ammonia is removed under a nitrogen current and then under high vacuum. The white residue, solid, is not purified.

(b) CYSTINOL (Described in the form of the dihydro chloride by J. C. Crawall et al., J. Chem. Soc. 4066-68 (1956) )

The preceding white residue is taken up by 400 cm$^3$ of distilled water and 1.5 g FeCl$_3$. A current of air is made to bubble through the solution obtained until the dissappearance of the thiol (sodium nitroprussiate test) which took several hours. The solution is filtered. The colourless filtrate is concentrated under vacuum to 75 cm$^3$, then passed through a column of activated Dowex 50 × 8. The product is eluted with 1N NH$_4$OH.

The ammoniacal eluants are evaporated under vacuum and the residue, taken up in 100 cm$^3$ of ether, is refluxed. Insolubles are dried under vacuum.

Yield: 83% — Melting Point: 71° to 73° (Tottoli) White crystals soluble in water, methanol, ethanol.

| Analysis for $C_6H_{16}O_2N_2S_2$ = 212.33 | | | | |
|---|---|---|---|---|
| C% | calculated | 33.94 | found | 34.02 to 34.29 |

-continued

| Analysis for $C_6H_{16}O_2N_2S_2$ = 212.33 | | | | |
|---|---|---|---|---|
| H | " | 7.59 | 7.78 | |
| N | " | 13.19 | " | 13.05 to 13.05 |
| S | " | 30.20 | " | 30.10 |

IR SPECTRUM: $NH_2$ band 1605 cm$^{-1}$; OH band 1074 – 1053 cm$^{-1}$.

| T.L.C.: Prepard silica gel plates 60F254; H = 8 cm | |
|---|---|
| n-Propanol | 60 |
| $NH_4OH$ | 30 |
| Ethylene Diamine | 10 |
| Developers: Ninhydrin - $I_2$ | |
| NMR SPECTRUM - Reference TMS | |
| —$\underline{CH_2}$OH | 3.55 p.p.m. (m) |
| | 3.15 p.p.m. (m) |
| $-\underset{|}{\overset{|}{C}}-H$ | |
| —$CH_2$—S— | 2.8 p.p.m. (m) |

EXAMPLE 7

Neutral Oxalate of
2,9-diamino-5,6-dithia-1,10-decanediol (homocystinol)

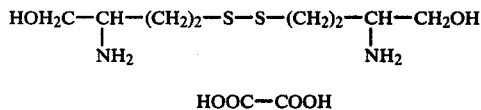

HOOC—COOH

To a solution of 5.3 g of S-benzylhomocysteinol in 250 ml of liquefied ammonia, there is added with mechanical stirring 1g (the theoretical amount) of sodium as fine flakes. The ammonia is evaporated at the laboratory temperature to two-thirds and the reaction mixture is treated with 2.67 g of $NH_4Cl$ added in small amounts, then evaporated.

The residue is taken up by 130 ml of water and 0.5 g of $FeCl_3$. Air is rapidly made to bubble through it for 5 hours. The thiol is then negative (nitroprussiate test).

The solution is passed over a 100 ml column of activated Dowex 50 × 8 (H = 70 cm, $\phi$ = 2 cm). The product is eluted by 2N ammonia and the eluate reduced to dryness.

The residual oil is solidified in ethyl acetate and the resulting powder brought for 15 minutes to reflux in ether then dried. Crude yield = 98%.

The compound is salified by the theoretical quantity of oxalic acid in an alcoholic medium.

The salt is purified by dissolving in the minimum quantity of water and the addition of ethanol up to the commencement of precipitation.

Yield : 35% — Melting Point : 205° to 207° (Tottoli).

| Analysis for $C_{10}H_{22}O_6N_2S_2$ = 330.42 | | | | |
|---|---|---|---|---|
| C% | calculated | 36.35 | found | 36.18 |
| H | " | 6.71 | " | 6.85 |
| N | " | 8.48 | " | 8.47 |
| S | " | 19.41 | " | 19.72 |

IR SPECTRUM : —COO— band 1575 cm$^{-1}$; OH band 1060 cm$^{-1}$.

| NMR SPECTRUM - Reference TMS | |
|---|---|
| $CH_2$—$CH_2$—CH | 2.1 p.p.m. (massive) |
| S—$CH_2$—$CH_2$ | 2.8 p.p.m. (massive) |
| $-\underset{CH_2OH}{\overset{|}{C}}-H$ ⎫⎬⎭ | 3.3 3.9 p.p.m. (massive) |

| T.L.C. Prepared silica gel plates 60F254 H = 8 cm | |
|---|---|
| Propanol | 60 |
| $NH_4OH$ | 30 |
| Ethylene Diamine | 10 |
| Developers - Ninhydrin - $I_2$ | |

EXAMPLE 8

Neutral oxalate of 2,10-diamino-5,7-dithia-1,11 undecanediol (homodjenkolol)

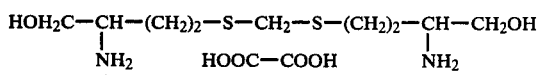

HOOC—COOH

To a solution of 10.5 g of S-benzylhomocysteinol in 500 ml liquefield ammonia there is added with stirring 2.3 g of sodium as flakes (the theoretical amount) then the theoretical quantity of dibromo methane (4.35 g). The blockage of the thiol is immediate. The excess of sodium amide is destroyed by 2.67 g of $NH_4Cl$ and the ammonia evaporated.

The residue is taken up by 200 ml of ether. Insolubles are extracted by 3 × 100 ml of ethyl acetate under reflux with stirring. The ethyl acetate solutions deposited 3.8 g (yield = 60%) crystals.

The product is salified in the form of the oxalate in absolute ethanol. It is purified by dissolving in the minimum of water and re-precipitation by ethanol. After 12 hours in an ice-box, 4.8 g of white crystals are collected.

Yield 56.8%.

Melting Point : 189°–190° (Tottoli) Soluble in water and alcohols.

| Analysis for $C_{11}H_{24}O_6N_2S_2$ = 344.45 | | | | |
|---|---|---|---|---|
| C% | calculated | 38.36 | found | 38.08 |
| H | " | 7.02 | " | 7.10 |
| N | " | 8.13 | " | 8.23 |
| S | " | 18.62 | " | 18.28 |

IR SPECTRUM : —COOH band:1580 cm$^{-1}$; OH bands:1073 cm$^{-1}$, 1300 cm$^{-1}$.

| NMR SPECTRUM - Reference TMS | |
|---|---|
| —S—$\underline{CH_2}$—S— | 3.82 p.p.m. (s) |
| $-\underline{CH_2}OH$ ⎫⎬⎭ $-\underset{|}{\overset{|}{C}}-H$ | |
| —S—$CH_2$—$CH_2$— | 2.8 p.p.m. (m) |
| —CH—$\underline{CH_2}$— | 2 p.p.m. (massive) |

| T.L.C. (silica gel prepared plates 60F354 H = 8 cm) | |
|---|---|
| Propanol | 60 |
| $NH_4OH$ | 30 |
| Ethylene Diamine | 10 |
| Developers: Ninhydrin - $I_2$ | |

EXAMPLE 9

Neutral oxalate of 2,11-diamino-5,8-dithia-1,12 dodecanediol $$HOH_2C-CH-(CH_2)_2-S-(CH_2)_2-S-(CH_2)_2-CH-CH_2OH$$
$$\phantom{HOH_2C-}|\phantom{CH-(CH_2)_2-S-(CH_2)_2-S-(CH_2)_2-}|$$
$$\phantom{HOH_2C-}NH_2 \quad\quad HOOC-COOH \quad\quad NH_2$$

The operative procedure of Example 8 is followed using double the theoretical quantity of dibromo methane. The blocking time of the thiol is 7 hours. After passage over a column of Dowex 50 × 8, the crude yield is 86%. The yield of purified neutral oxalate is 40%. The white crystals obtained are soluble in water and alcohols.

Melting Point 194°–195.5° (d) (Tottoli).

| Analysis for $C_{12}H_{26}O_6N_2S_2 = 358$ | | | | |
|---|---|---|---|---|
| C% | calculated | 40.20 | found | 39.94 |
| H | " | 7.31 | " | 7.52 |
| N | " | 7.81 | " | 8.15 |
| S | " | 17.89 | " | 17.71 |

IR SPECTRUM : —COOH band:1626 cm$^{-1}$; OH bands:1060 cm$^{-1}$ and 1300 cm$^{-1}$.

NMK SPECTRUM - Reference $HOH_2C-$
$\phantom{HO}|$
$-C-\underline{H}$ : 3.4 to 3.9 p.p.m. (massive)
$\phantom{HO}|$ $-S-(CH_2)_2-S-$ : 2.83 p.p.m. (s)
$-S-\underline{CH_2}-CH_2$ : 2.7 p.p.m. (m)
$-\underline{CH_2}-CH-$ : 2 p.p.m. (massive)
$\phantom{-CH_2-CH}|$ T.L.C. Prepared silica gel plates 60F254
H = 8 cm
Propanol 60
NH$_4$OH 30
Ethylene Diamine 10
Developers: Ninhydrin - I$_2$

EXAMPLE 10

Mandelate of 2,13-diamino-5,10-dithia-1,14-tetradecanediol $$HOH_2C-CH-(CH_2)_2-S-(CH_2)_4-S-(CH_2)_2-CH-CH_2OH$$
$$\phantom{HOH_2C-}|\phantom{CH-(CH_2)_2-S-(CH_2)_4-S-(CH_2)_2-}|$$
$$\phantom{HOH_2C-}NH_2, \quad (HOOC-CHOH-C_6H_5)_2 \quad NH_2$$

Following always the same operative procedure using the theoretical quantity of 1,4-dibromo-butane, the blockage of the SH groups is obtained in 15 minutes. After extraction by dichloromethane and recrystallisation in ethyl acetate the yield of the impure base is 45%.

The base is salified in ethanol and the neutral mandelate obtained washed with ether. The white crystals obtained are soluble in water, alcohols and dimethylformamide.

M.Pt. 153° (Tottoli) — Yield : 29%.

| Analysis for $C_{28}H_{44}O_8N_2S_2 = 600.79$ | | | | |
|---|---|---|---|---|
| C% | calculated | 55.97 | found | 56.26 |
| H | " | 7.38 | " | 7.66 |
| N | " | 4.66 | " | 4.58 |
| S | " | 10.67 | " | 10.93 |

IR SPECTRUM - —COOH band:1577 cm$^{-1}$; OH bands:1064 cm$^{-1}$, 1355 cm$^{-1}$.

NMR SPECTRUM - Reference TMS

C$_6$H$_6$ ring : 7.4 p.p.m. (s)

C$_6$H$_5$—CH— : 4.95 p.p.m. (s)

—CH$_2$OH : 3.6 p.p.m. (m)

$-\underline{C}H-$ : 3.3 p.p.m (massive)
$\phantom{-C}|$

—C$\underline{H_2}$—S—C$\underline{H_2}$— : 2.5. p.p.m. (massive)

$-(CH_2)_2-$
$-C\underline{H_2}-\underset{|}{C}-H$ : 1.5 to 2 p.p.m.(massive)

T.L.C. Prepared silica gel plates 60F254
H = 8 cm
Propanol 60
NH$_4$OH 30
Ethylene Diamine 10
Developers: Ninhydrin - I$_2$

EXAMPLE 11

Mandelate of 2,14-diamino-5,11-dithia-1,15-pentadecanediol $$HOH_2C-CH-(CH_2)_2-S-(CH_2)_5-S-(CH_2)_2-CH-CH_2OH$$
$$\phantom{HOH_2C-}|\phantom{CH-(CH_2)_2-S-(CH_2)_5-S-(CH_2)_2-}|$$
$$\phantom{HOH_2C-}NH_2 \quad (HOOC-CHOH-C_6H_5)_2 \quad NH_2$$

Following the operative procedure of Example 8, an excess of 5% over the theoretical quantity of 1,5-dibromopentane is used. The blockage time of the SH-group is 5 hours. Extraction is carried out by dichloromethane and the product recrystallised in ethyl acetate. The yield of impure base is 63%. The mandelate is prepared in ethanol and washed with ether.

Yield : 49.5% — M.Pt. : 131°–132° C. (Tottoli) Soluble in water, alcohols, DMF.

| Analysis for $C_{29}H_{46}O_8N_2S_2 = 614.82$ | | | | |
|---|---|---|---|---|
| C% | calculated | 56.65 | found | 56.81 |
| H | " | 7.54 | " | 7.75 |
| N | " | 4.55 | " | 4.64 |
| S | " | 10.43 | " | 10.38 |

IR SPECTRUM : —COOH band : 1587 cm$^{-1}$. OH bands : 1064 cm$^{-1}$, 1351 cm$^{-1}$.

NMR SPECTRUM: Reference TMS

| Group | Shift |
|---|---|
| C$_6$H$_5$– | 7.4 p.p.m. (s) |
| C$_6$H$_5$–CH | 4.95 p.p.m. (s) |
| –CH$_2$OH | 3.6 p.p.m. (massive) |
| –C–H | 3.3 p.p.m. (massive) |
| –CH$_2$–S–CH$_2$– | 2.5 p.p.m. (massive) |
| –(CH$_2$)$_3$–<br>–CH$_2$–C–H | 1.3 to 2 p.p.m. (massive) |

T.L.C. Prepared plates 60F254 H = 8 cm
Propanol           60
NH$_4$OH           30
Ethylene diamine   10
Developers: Ninhydrin -I$_2$

EXAMPLE 12

2,15-Diamino-5,12-dithia-1,16-hexadecanediol

HOH$_2$C—CH—(CH$_2$)$_2$—S—(CH$_2$)$_6$—S—(CH$_2$)$_2$—CH—CH$_2$OH
      |                                          |
      NH$_2$                                     NH$_2$

Following the operative procedure of Example 8 there is obtained, using the theoretical quantity of 1,6-dibromohexane, a thiol blockage time of 15 minutes. After extraction by dichloromethane and recrystallisation in ethyl acetate white crystals are obtained.

M.Pt. : 79°-81° (Kofler) — Yield : 61%. White crystals soluble in water and alcohols.

| Analysis for C$_{14}$H$_{32}$O$_2$N$_2$S$_2$ = 324.55 | | | | |
|---|---|---|---|---|
| C% | calculated | 51.81 | found | 51.80 – 51.52 |
| H | " | 9.44 | " | 10.23 – 10.30 |
| N | " | 8.63 | " | 8.67 |
| S | " | 19.76 | " | 19.52 |

IR SPECTRUM : NH$_2$ band : 1550 cm$^{-1}$; OH bands : 1060 cm$^{-1}$, 1350 cm$^{-1}$.

NMR SPECTRUM - Reference TMS

| Group | Shift |
|---|---|
| –(CH$_2$)$_4$–<br>–CH$_2$–C–H | 1.6 p.p.m. (massive) |
| 2–CH$_2$OH | 3.5 p.p.m. (m) |
| 4–CH$_2$–S– | 2.6 p.p.m. (m) |
| –C–H | 3 p.p.m. (massive) |

T.L.C. Prepared plates 60F 254 H = 8 cm
       n-Butanol         40
       Ethylene diamine  50
       Acetic acid       10
       Developers: Ninhydrin -I$_2$

EXAMPLE 13

2,17-Diamino-5,14-dithia-1,18-octadecanediol

HOH$_2$C—CH—(CH$_2$)$_2$—S—(CH$_2$)$_8$—S—(CH$_2$)$_2$—CH—CH$_2$OH
      |                                          |
      NH$_2$                                     NH$_2$

Following the operative procedure of Example 8 there is obtained using the theoretical quantity of 1,8-dibromo-octane blockage of the thiol in one hour. Extraction is carried out by dichloromethane and recrystallisation in ethyl acetate.

M.Pt. : 84° C. (Kolfer) — Yield : 28% White crystals soluble in water and alcohols.

| Analysis for C$_{16}$H$_{36}$O$_2$N$_2$S$_2$ = 352.6 | | | | |
|---|---|---|---|---|
| C% | calculated | 54.50 | found | 54.42 |
| H | " | 10.29 | " | 10.42 |
| N | " | 7.94 | " | 7.87 |
| S | " | 18.18 | " | 17.95 |

IR SPECTRUM : NH$_2$ band: 1560 cm$^{-1}$; OH bands: 1064 cm$^{-1}$, 1345 cm$^{-1}$.

NMR SPECTRUM

| Group | Shift |
|---|---|
| –CH$_2$–CH–<br>–(CH$_2$)$_6$– | 1.6 p.p.m. (massive) |
| 2-CH$_2$–OH | 3.5 p.p.m. (m) |
| 4-CH$_2$–S– | 2.6 p.p.m. (m) |
| 2-CH | 3 p.p.m. (massive) |

T.L.C. Prepared plates 60F 254 H = 8 cm
       Propanol          60
       NH$_4$OH          30
       Ethylene diamine  10
       Developers: Ninhydrin -I$_2$

EXAMPLE 14

2,19-Diamino-5,16-dithia-1,20-eicosanediol

HOH$_2$C—CH—(CH$_2$)$_2$—S—(CH$_2$)$_{10}$—S—(CH$_2$)$_2$—CH—CH$_2$OH
      |                                            |
      NH$_2$                                       NH$_2$

Following the operative procedure of Example 8 and using an excess of 20% relative to the theoretical quantity of 1,10-dibromo-decane, the blockage of the thiol is effected in 2 hours 30 minutes. The product is extracted with dichloromethane and recrystallised in ethyl acetate.

Yield : 27% — White crystals soluble in water and alcohols.

| Analysis for C$_{18}$H$_{40}$O$_2$N$_2$S$_2$ = 380.59 | | | | |
|---|---|---|---|---|
| C% | calculated | 56.79 | found | 56.87 |
| H | " | 10.59 | " | 10.71 |
| N | " | 7.36 | " | 7.07 |
| S | " | 16.85 | " | 16.76 |

IR SPECTRUM NH$_2$ band : 1550 cm$^{-1}$; OH bands : 1060 cm$^{-1}$ – 1350 cm$^{-1}$.

NMR SPECTRUM $-(C\underline{H}_2)_8-$ ⎫
$-C\underline{H}_2-\underset{|}{\overset{|}{C}}-\underline{H}$ ⎬ 1.5 p.p.m. (massive)

4-C$\underline{H}_2$—S—  2.6 p.p.m. (m)
2-C$\underline{H}_2$OH  3.4 p.pm. (m)
                   2.9 p.p.m. (massive)

2-$\underset{|}{\overset{|}{C}}$—$\underline{H}$

T.L.C. Prepared plates 60F 254 H = 8 cm
       Propanol          60
       NH$_4$OH          30
       Ethylene diamine  10
Developers: Ninhydrin -I$_2$

Pharmacological Study

The compounds of the invention were subjected to various tests with a view to determining their therapeutic activity.

TOXICITY

The products of the invention are hardly toxic.

The oral LD 50 (see the table below) was determined according to the method of Karber and Behrens (Arch. Exp. Pathol. Pharm. 177, 1935, page 379) on mice EVIC CEBA ♀ Swiss EOPS NMRI Han of 24 to 26 g weight.

The results are given in the table below.

HYPOLIPEMIC : HYPERLIPIDEMIC ACTIVITY EXPERIMENTALLY INDUCED BY TRITON

The compounds of the invention possess useful hypolipemic properties.

The technique used to show these properties has been described by M. Friedman and S. E. Byers in : J. Exptl. Med. 97, 117, 1953 and likewise by S. Garattini and colleagues in Arzneim. Forsch. 9, 206, 1959.

The rats received intravenously 0.3 ml per 100 grams of body weight of a solution of Triton 13 39 at 10%. The products to be tested are administered simultaneously orally at a dose corresponding to a tenth of their LD 50, determined orally in mice, without the dose used exceeding 500 mg/kg.

Eighteen hours after the injection of Triton the animals are sacrificed by section of the carotid and the blood is collected to determined the lipid parameters : cholesterol (auto-analyser Technicon AA II Lieberman Burchard), beta- lipoproteins, (Burnstein), total lipids (Chabrol and Charonnat), triglycerides (Boehringer enzymatic).

The optical density of the serum at 691 nanometres is measured in each case. Each product was tested on ten animals. The statistic calculations were carried out on the averages affected by their divergence from the average using the Student test.

The reference compound used is clofibrate.
The table below sets out the results obtained.

TABLE

| Compound | LD 50 g/kg per os | Dose mg/kg p.o. | Hypolipemic activity percentages of diminution | | | | |
|---|---|---|---|---|---|---|---|
| | | | Cholesterol | β-lipoprotein | total lipids | Triglycerides | optical serum density |
| Clofibrate | 2,3 | 225 | 28 $p \leq 0.001$ | 36 $p \leq 0.01$ | 26 $p \leq 0.001$ | 25 $p \leq 0.001$ | — |
| Example 1 | >5 | 500 | 10 $p \leq 0.05$ | NS | NS | NS | NS |
| Example 2 | 5 | 500 | NS | NS | NS | 14 $p \leq 0.05$ | NS |
| Example 3 | 2.7 | 270 | 4 NS | 39 $p \leq 0.01$ | 27 $p \leq 0.001$ | 28 $p \leq 0.001$ | 53 $p \leq 0.01$ |
| Example 4 | 1.275 | 127 | 10 $p \leq 0.01$ | 24 $p \leq 0.01$ | NS | 34 $p \leq 0.001$ | 57 $p \leq 0.001$ |
| Example 5 | 1.75 | 175 | 8 $p \leq 0.02$ | NS | NS | 30 $p \leq 0.01$ | 56 $p \leq 0.01$ |
| Example 6 | 3.1 | 310 | 40 $p \leq 0.0001$ | 46 $p \leq 0.0001$ | 38 $p \leq 0.001$ | 42 $p \leq 0.0001$ | 78 $p \leq 0.0001$ |
| Example 12 | 2.5 | 250 | NS | 11 $p \leq 0.01$ | NS | NS | NS |
| Example 13 | 1.4 | 140 | 13 $p \leq 0.02$ | 23 $p \leq 0.001$ | 27 $p \leq 0.01$ | 33 $p \leq 0.01$ | 48 $p \leq 0.05$ |
| Example 14 | 0.95 | 95 | NS | 15 $p \leq 0.001$ | NS | NS | NS |

NS : non-significant result

These compounds which can be administered orally are suggested for use in the treatment of lipid disturbances isolated or associated with atherosclerotic symptoms such as hypercholesterolemias, hypertriglyceridemias and mixed hyperlipidemias. The therapeutic indications tend to myocardial coronary infarctus, insufficient cerebral vasculation, arteritis of the lower members, arterial hypertension etc.

The dose of the compounds of the invention is of the order of 0.3 g to 2 g of active substance per day, i.e. 5 to 30 mg/kg per day.

The compound of the invention can be administered in various pharmaceutical forms such as tablets, dragees capsules, granules etc.

Examples of pharmaceutical compositions are given below:

| Lozenges : | |
|---|---|
| Compound of Example 6 | 250 mg |
| Colloidal silica | 20 mg |
| Talc | 15 mg |
| Tablets : | |
| Compound of Example 6 | 500 mg |
| Colloidal silica | 20 mg |
| Microcrystalline cellulose | 50 mg |
| Lactose | 50 mg |
| Magnesium stearate | 10 mg |

We claim:

1. A pharmaceutical composition useful in the treatment of lipid disturbances which comprises, as active ingredient a hypolipemic amount of, a compound corresponding to the general formula I $$HOH_2C-\underset{NH_2}{CH}-(CH_2)_{\overline{m}}-S-(CH_2)_{\overline{n}}-S-(CH_2)_{\overline{m}}-\underset{NH_2}{CH}-CH_2OH \quad (I)$$

in which n is equal to 0 or represents a whole number from 1 to 10 and m represents the number 1 or 2 or a pharmacologically acceptable salt of such a compound, together with a pharmacologically acceptable carrier or diluent.

2. A pharmaceutical composition according to claim 1 wherein the ctive ingredient is selected from the group consisting of:
   2,8-diamino-4,6-dithia-1,9-nonanediol,
   2,11-diamino-4,9-dithia-1,12-dodecanediol,
   2,13-diamino-4,11-dithia-1,14-tetradecanediol,
   2,15-diamino-4,13-dithia-1,16-hexadecanediol,
   2,17-diamino-4,15-dithia-1,18-octadecanediol,
   2,7-diamino-4,5-dithia-1,8-octanediol,
   2,15-diamino-5,12-dithia-1,16-hexadecanediol,
   2,17-diamino-5,14-dithia-1,18-octadecanediol,
   2,19-diamino-5,16-dithia-1,20-eicosanediol,
   and their pharmacologically acceptable salts 3. A pharmaceutical composition according to claim 1 which is in an orally administrable form.

4. A pharmaceutical composition according to claim 3 which is in a form permitting administration of doses of from 5 to 30 mg/kg per day.

5. A method of treating a human patient afflicted with a lipid disturbance which method comprises administering to the patient a hypolipemic amount of a compound of formula I $$HOH_2C-\underset{NH_2}{CH}-(CH_2)_{\overline{m}}-S-(CH_2)_{\overline{n}}-S-(CH_2)_{\overline{m}}-\underset{NH_2}{CH}-CH_2OH \quad (I)$$

in which n is equal to 0 or represents a whole number from 1 to 10 and m represents the number 1 or 2 or a pharmacologically acceptable salt thereof.

6. The method of claim 5, wherein the compound is selected from the Group consisting of:
   2,8-diamino-4,6-dithia-1,9-nonanediol,
   2,11-diamino-4,9-dithia-1,12-dodecanediol,
   2,13-diamino-4,11-dithia-1,14-tetradecanediol,
   2,15-diamino-4,13-dithia-1,16-hexadecanediol,
   2,17-diamino-4,15-dithia-1,18-octadecanediol,
   2,7-diamino-4,5-dithia-1,8-octanediol,
   2,15-diamino-5,12-dithia-1,16-hexadecanediol,
   2,17-diamino-5,14-dithia-1,18-octadecanediol,
   2,19-diamino-5,16-dithia-1,20-eicosanediol, and their pharmacologically acceptable salts.

7. The method of claim 5, wherein the compound is administered orally.

8. The method of claim 7, wherein the compound is administered in a dose of five to thirty mg/kg per day.

* * * * *

UNITED STATES PATENT AND TRADEMARK OFFICE
CERTIFICATE OF CORRECTION

PATENT NO. : 4,153,729

DATED : May 8, 1979

INVENTOR(S) : Warolin et al.

It is certified that error appears in the above-identified patent and that said Letters Patent are hereby corrected as shown below:

Col. 7, line 55; "-4($CH_2)_6$" should read -- -$(CH_2)_6$ --
Col. 8, line 22; "playtes" should read -- plates --
Col. 9, line 11; "Prepard" should read -- Prepared --
Col. 11, line 28; "NMK SPECTRUM - Reference" should read -- NMR SPECTRUM - Reference TMS --
Col. 14, line 14; "(Kolfer)" should read -- (Kofler) --
Col. 16, line 5; "determined" should read -- determine --
Col. 16, line 54; "compound" should read -- compounds --
Col. 17, line 18; "ctive" should read -- active --

Signed and Sealed this

Second Day of October 1979

[SEAL]

Attest:

RUTH C. MASON
*Attesting Officer*

LUTRELLE F. PARKER
*Acting Commissioner of Patents and Trademarks*